(12) United States Patent
Keenan

(10) Patent No.: US 7,329,531 B2
(45) Date of Patent: Feb. 12, 2008

(54) BLOOD-TIGHT IMPLANTABLE TEXTILE MATERIAL AND METHOD OF MAKING

(75) Inventor: Steve Keenan, Watertown, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 673 days.

(21) Appl. No.: 10/734,785

(22) Filed: Dec. 12, 2003

(65) Prior Publication Data

US 2005/0131531 A1    Jun. 16, 2005

(51) Int. Cl.
*C12N 1/00* (2006.01)
(52) U.S. Cl. ..................................... 435/243
(58) Field of Classification Search ................ 524/13; 523/204, 205, 206, 207, 215, 216; 428/372
See application file for complete search history.

(56) References Cited

U.S. PATENT DOCUMENTS

| | | |
|---|---|---|
| 4,167,045 A | 9/1979 | Sawyer |
| 4,369,069 A | 1/1983 | Graesser et al. |
| 4,416,814 A | 11/1983 | Battista |
| 4,787,900 A | 11/1988 | Yannas |
| 4,791,063 A * | 12/1988 | Hou et al. ................ 435/243 |
| 5,028,597 A | 7/1991 | Kodama et al. |
| 5,108,424 A | 4/1992 | Hoffman, Jr. et al. |
| 5,135,744 A | 8/1992 | Czech et al. |
| 5,144,016 A | 9/1992 | Skjak-Braek et al. |
| 5,209,776 A | 5/1993 | Bass et al. |
| 5,336,501 A | 8/1994 | Czech et al. |
| 5,360,828 A | 11/1994 | Morrison |
| 5,415,619 A | 5/1995 | Lee et al. |
| 5,573,934 A | 11/1996 | Hubbell et al. |
| 5,584,875 A | 12/1996 | Duhamel et al. |
| 5,843,743 A | 12/1998 | Hubbell et al. |
| 5,851,229 A | 12/1998 | Lentz et al. |
| 5,854,382 A | 12/1998 | Loomis |
| 6,005,020 A | 12/1999 | Loomis |
| 6,028,164 A | 2/2000 | Loomis |
| 6,364,893 B1 | 4/2002 | Sahatjian et al. |
| 6,540,780 B1 | 4/2003 | Zilla et al. |
| 6,589,199 B1 | 7/2003 | McCrory et al. |

(Continued)

FOREIGN PATENT DOCUMENTS

FR        2 793 693        11/2000

(Continued)

OTHER PUBLICATIONS

Development and Characterization of Alginate-Impregnated Polyester Vascular Graft. Lee. J. H. et al., Journal of Biomedical Materials Research, Aug. 1997 36 (2), p. 200-8.

(Continued)

*Primary Examiner*—Kevin T. Truong
(74) *Attorney, Agent, or Firm*—Hoffman & Baron, LLP

(57) ABSTRACT

An unmodified textile material is combined with a mixture including a non-colloidal polysaccharide slurry to form a blood-tight implantable textile material. A substantially porous unmodified textile material is impregnated with a biocompatible, bioresorbable slurry to make an implantable textile material, preferably in the form of a vascular graft. Sodium alginate is a preferred polysaccharide to use in the mixture, which serves as a viable alterative to collagen impregnation and coatings of vascular grafts.

19 Claims, 4 Drawing Sheets

U.S. PATENT DOCUMENTS 6,632,446 B1    10/2003    Hubbell et al.

FOREIGN PATENT DOCUMENTS

WO    WO 01/17571    3/2001

OTHER PUBLICATIONS

Small Caliber Vascular Grafts, Part I: State of the Art, Zdrahala, R.J., Journal of Biomaterials Applications, Apr. 1996, 10 (4) p. 309-29.

Dutkiewicz; Some Uses of Krill Chitosan as Biomaterial; Chem. Biochem. Phys. Prop. Appl. Proceedings of the International Conference, Elsevier Science Publishers Ltd., London, GB, 1989 pp. 719-730; XP0087461.

Lee et al; Development and characterization of an alginate-impregnated polyester vascular graft; Journal of Biomedical Materials Research, Wiley, New York, vol. 36, No. 2, Aug. 1997, pp. 200, 201; XP00874531.

Viscardi, et al.; Iloprost and alginate decreases the thrombogenicity of expanded polytetrafluoroethylene; Journal of Reconstructive Microsurgery, New York, vol. 13, No. 4, May 1997 pp. 303-306; XP00874664.

Koseki M. et al.; Determination of Pectin in the presence of food polysaccharides; Journal of Food Science, vol. 51, No. 5; 1986, pp. 1329-1332; XP002325640.

\* cited by examiner

BLOOD-TIGHT IMPLANTABLE TEXTILE MATERIAL AND METHOD OF MAKING

FIELD OF THE INVENTION

The present invention relates generally to the art of implantable medical prostheses. More particularly, the present invention relates to the creation of a textile material with improved blood-tight properties, decreased porosity, and a more simplified process of making the implantable material.

BACKGROUND OF THE INVENTION

Implantable prostheses are commonly used in medical applications. One of the more common prosthetic structures include tubular prostheses which may be used as vascular grafts to replace or repair damaged or diseased blood vessels. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting, or braiding synthetic fibers into a tubular configuration. Tubular textile structures have the advantage of being naturally porous which allows desired tissue in-growth and assimilation into the body. This porosity, which allows for in-growth of surrounding tissue, must be balanced with fluid tightness so as to minimize leakage during the initial implantation stage.

Attempts to control the porosity of the graft while providing a sufficient fluid barrier have focused on increasing the thickness of the textile structure, providing a tighter stitch construction, and including features such as velours to the graft structure. It is also known to form a prosthesis, especially tubular grafts, from polymers such as polytetrafluoroethylene (PTFE). A tubular graft may be formed by stretching and expanding PTFE into a structure referred to as expanded polytetrafluoroethylene (ePTFE). Grafts formed from ePTFE overcome certain disadvantages inherent in textile grafts, such as that they are more fluid-tight. ePTFE grafts however are not as compliant as textile grafts.

Alternatively, it is also known to apply a natural coating, such as collagen or gelatin to a textile graft in order to render it more blood-tight. Collagen or gelatin impregnation of a graft is another method to render the graft blood-tight. It is desirable that a vascular graft ultimately be sufficiently blood-tight to prevent the loss of blood during implantation, yet also be sufficiently porous to permit in-growth of fibroblast and smooth muscle cells in order to attach the graft to the host tissue and ensure a successful implantation and adaptation within the host body.

Collagen reinforced grafts include collagen obtained from deep flexer tendon of cattle. Tendon derived collagen is generally highly cross-linked and difficult to process by the enzyme digestion procedure described in the patent. The difficulties in processing the collagen lead to increased manufacturing time and expense and decrease commercial viability.

Collagen fibrils may also be mixed with a plasticizer which renders the graft blood-tight. It is preferably done with a Dacron® vascular graft material which may be woven or knit. The collagen source is preferably from bovine skin which has been processed by an acid digestion to result in a fibril dispersion of high purity. The processing steps again are a drawback to the use of collagen coatings.

In addition to the above-mentioned drawbacks associated with collagen, there are also problems relating to the source of the material. Collagen is typically derived from animal sources, primarily from cows. Because of the high demand for resources from cows and other bovines, there is a need to provide an alternate source of biocompatible materials to use for such a coating. Particularly, in light of Bovine Spongiform Encephalopathy, and the threat it poses to cattle worldwide, there is a limited supply of bovine sources.

As an additional alternative, porous vascular graft materials have been pretreated with blood prior to introduction of the graft into the body. Such a pretreatment introduces clotting factors throughout the graft that help to reduce bleeding during surgery by causing blood to become clotted before significant loss of blood to the patient occurs. Generally, these grafts are immersed in, or flushed with, fresh blood of the patient in order to preclot the surfaces of the graft. These methods are limited because they are time consuming, require blood transfusions from the patient, and increase the amount of blood loss from the patient. Thus, such methods are not available in emergency medical situations where the patient has lost a large amount of blood or where time is a critical factor. In addition, such methods cannot be used effectively with patients who are taking anticoagulants, such as heparin or warfarin.

A considerable amount of research has centered around developing materials that are initially blood-tight and then gradually become more porous in order to facilitate healing and tissue ingrowth into the implanted graft. Much of this research has focused on coating the surfaces of porous graft materials with extracellular matrix (ECM) proteins in order to render such graft materials blood-tight, but which, over time biodegrade and promote tissue ingrowth into the graft. As previously stated, collagen, albumin, gelatin, elastin, and fibrin have all been used as bioresorbable sealants for porous vascular grafts.

In addition, gels, hydrogels and sol-gels have also been described as biocompatible, biodegradable materials. A gel is a substance with properties intermediate between the liquid and solid states. Gels deform elastically and recover, yet will often flow at higher stresses. They have extended three-dimensional network structures and are highly porous. Accordingly, many gels contain a very high proportion of liquid to solid. The network structures can be permanent or temporary and are based on polymeric molecules, basically formed from a colloidal solution on standing. Thus, a hydrogel may be described as a gel, the liquid constituent of which is water. By way of contrast, a sol is a colloidal solution, i.e., a suspension of solid particles of colloidal dimensions in a liquid. See, Larouse Directory of Science and Technology 470, 543 (1995).

The bonding of separated tissues together or the coating of the surface of tissues or prosthetic materials to form a water-tight seal is also known. A first protein component is preferably a collagen and a second protein-supporting component that can be a proteoglycan, a saccharide or a polyalcohol. In this composition, the second component is adapted to support the first component by forming a matrix, sol or gel with the first component. Thus, the matrix, sol or gel formed is a hybrid composition that includes a protein component and a protein-supporting component that can be a protein, a saccharide or a polyalcohol. The protein component provides the sealing or bonding function, while the protein-supporting component forms a supporting matrix for the protein.

Hydrogels may be used as wound secretion absorbers or incorporated into wound dressings for absorbing wound secretions. The hydrogel composition of these inventions include 20-70% of at least one multivalent alcohol, for example glycerol, 10-35% of at least one natural biopolymer thickener agent, 0.05-10% of a cross-linking agent and 0-50% of water or physiological saline.

Such hydrogels can be gelatin alone or gelatin in combination with a polysaccharide, particularly an alginate. The hydrogel can be a protein hydrogel or a protein-polysaccharide hybrid hydrogel. In addition to gelatin, collagens and pectins are also preferred protein components in the hydrogel materials. However, protein materials are required to provide the sealing function and the hydrogels are used as carriers for the proteins.

Such hybrid coating compositions are not easily manufactured. For example, the protein components of the hybrid coating compositions can become denatured during the manufacturing, sterilizing or storing of the hydrogel coated material. Once denatured, these hybrid coating compositions can lose their ability to function. Another problem with such hybrid coating compositions is that the surface of the substrate material, e.g., wound dressing or implantable device, must be pretreated with, for example, plasma, in order to effectively bind such compositions to the surface of, for example, a vascular graft. In addition, such hybrid compositions are deposited as coatings on the surface of a substrate material. Such surface coatings are limited in that they are readily accessible to the body's degradative enzymes and thus are swiftly degraded.

There have been attempts to make grafts blood-tight by utilizing substances other than collagen or other proteinaceous material such as by manufacturing a vascular graft impregnated with polysaccharides. This method however requires a chemical or physical pretreatment of the graft in order to modify the graft and make it hydrophilic. The pretreatment of the graft consists of a chemical treatment with sulfuric acid or perchloric acid, or a physical treatment where the fabric surface of the graft is treated with plasma or corona discharge. The goal of the treatment is to make the graft hydrophilic by acquiring an ionic charge, or introducing hydroxyl groups on the fabric surface. After pretreatment, the graft is then coated or impregnated with the polysaccharide. Although this method alleviates the problem of protein denaturation during the manufacturing, sterilizing and storing of, for example, a vascular graft, the surface of such a graft must be chemically or physically altered in order to bind the polysaccharide coating to the surface thereof, for example, by chemically oxidizing the surface of a porous vascular graft with a solution of sulfuric or perchloric acid prior to impregnating the surface of the graft with a polysaccharide solution. Alternatively, the surface of such a graft may be physically altered by pretreatment with plasma or corona discharge. In either case, these methods add additional unnecessary steps to such a process by chemically or physically pretreating the surface of such vascular grafts.

A known bioresorbable sealant composition for an implantable prosthesis includes the combination of at least two polysaccharides which form a hydrogel that imparts a substantially blood-tight barrier to the prosthesis. This requires the combination of at least two polysaccharides, or a polysaccharide and a protein to form a hydrogel.

SUMMARY OF THE INVENTION

The present invention provides a blood-tight textile material implantable in a mammal. The blood-tight textile material may comprise an unmodified textile material having a porous structure. A biocompatible non-colloidal mono-polymeric mixture may be saturated within the porous structure of the textile material to make it substantially non-porous. The non-colloidal biocompatible mixture may comprise a polysaccharide, an alcohol, and water. The biocompatible mixture forms a slurry which is easily saturated or impregnated within the textile material by massaging the mixture in the pores.

A method of making a blood-tight implantable textile material may be also provided herein. An unmodified textile material is initially provided. A biocompatible non-colloidal mono-polymeric mixture may be formed by mixing a polysaccharide with water and an alcohol to form a mixture. The mixture may be saturated within the porous textile material to form the implantable textile material. In a preferred embodiment the implantable textile is a tubular structure and is used as a vascular graft.

BRIEF DESCRIPTION OF THE DRAWINGS

FIGS. 4A-4C are schematic showings of various types of braids that can be used as the textile material of the present invention. FIG. 4A depicts a diamond braid, FIG. 4B depicts a regular braid, FIG. 4C depicts a Hercules braid.

DETAILED DESCRIPTION OF THE PREFERRED EMBODIMENTS

While this invention may be satisfied by embodiments in many different forms, there will be described herein in detail preferred embodiments of the invention, with the understanding that the present disclosure is to be considered as exemplary of the principles of the invention and is not intended to limit the invention to the embodiments illustrated and described.

The present invention relates to blood-tight textile implantable materials and the simplified process of making the same. In particular, the blood-tight textile implantable material of the present invention may be an unmodified textile material having a porous structure. A biocompatible non-colloidal mixture is saturated within the porous structure of the textile material to make it substantially non-porous and blood-tight. The biocompatible mixture comprises a polysaccharide, an alcohol, and water. Preferably the alcohol is ethanol. The biocompatible mixture forms a slurry which is easily saturated or impregnated within the textile material by massaging the mixture within the porous structure.

The phrase "non-colloidal mon-polymeric" as used herein refers to a mixture which has only one polymer included therein. More particularly, a non-colloidal mixture does not include gels, hydrogels, sols, sol-gels, or any composition wherein more than one polymer is included therein. In a preferred embodiment a polysaccharide is mixed with an alcohol and water to make a slurry which is easily massaged in the porous structure of a textile material. The term "unmodified textile material" as used herein refers to a textile material which has not been physically or chemically treated in order to make the textile material more hydrophilic.

The textile material of the present invention may be chosen from a number of different textile structures. Textiles generally share a common quality that they are sufficiently porous to allow substantial ingrowth, particularly on the exterior surface of the lumen in order to allow accommodation in a host body by endothelial cells and the like. The natural drawback however is that the porous structure is not initially blood-tight and hemorrhaging occurs. The present invention addresses that problem by providing a biocompatible mixture which makes the textile material substantially non-porous and blood-tight. Examples of textile material which may be employed in the present invention include woven textile, knitted textiles, braided textiles, velours, and felt.

Figure 1:
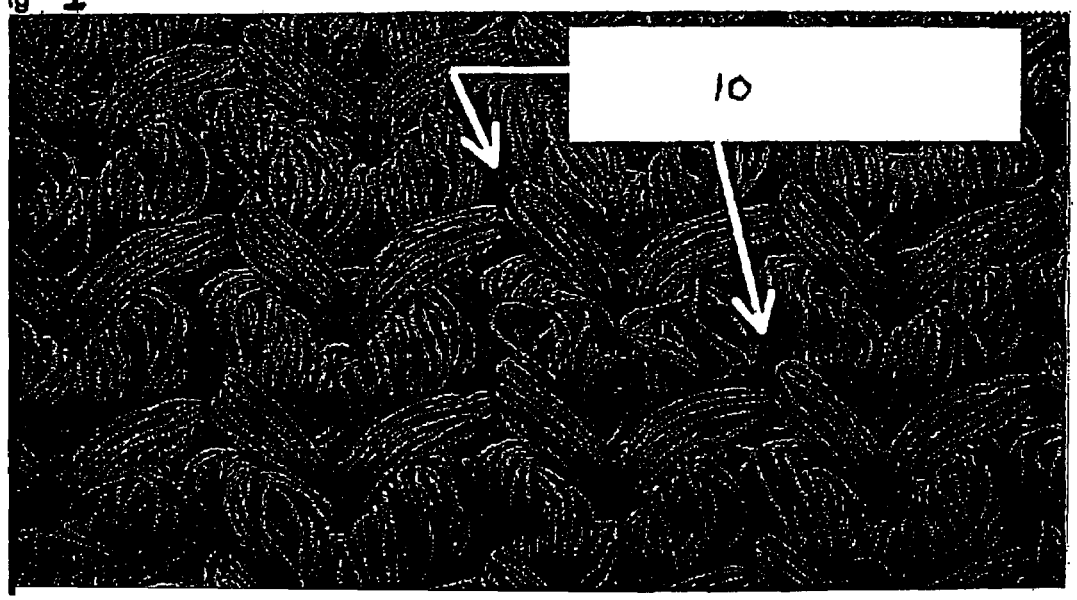
FIG. 1 is a photomicrograph of a woven double velour vascular graft which is a textile material as contemplated within the present invention.

With reference now to the figures, FIG. 1 shows a photomicrograph of a woven double velour vascular graft. Mircopores 10 can be seen within the double velour structure. The double velour graft shown in FIG. 1 is saturated or impregnated with a non-colloidal mixture which saturates mircropores 10 in order to provide a blood-tight textile material, prosthesis, or more particularly a blood-tight artificial vascular graft.

Figure 2:
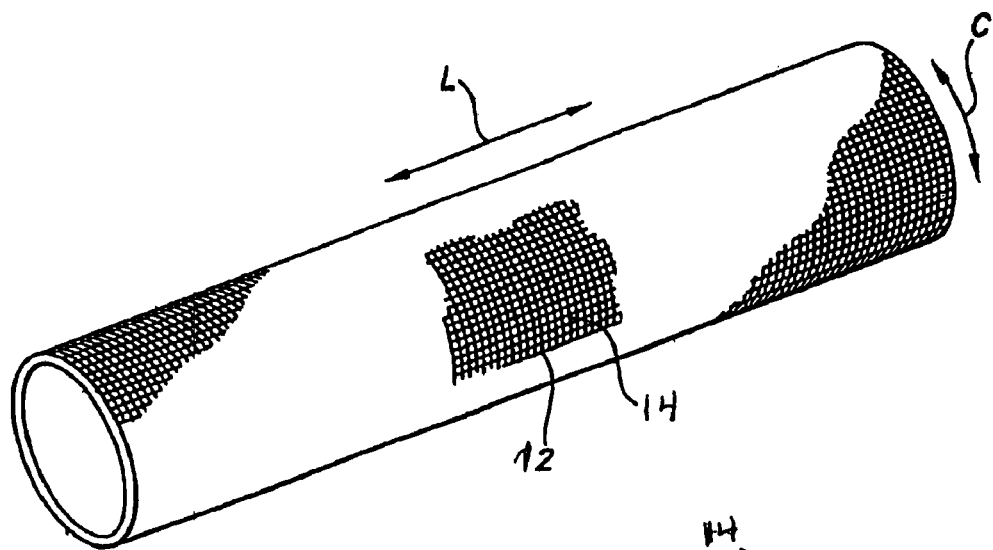
FIG. 2 is a perspective view of a vascular graft with a textile structure as used in the present invention.
Figure 3:
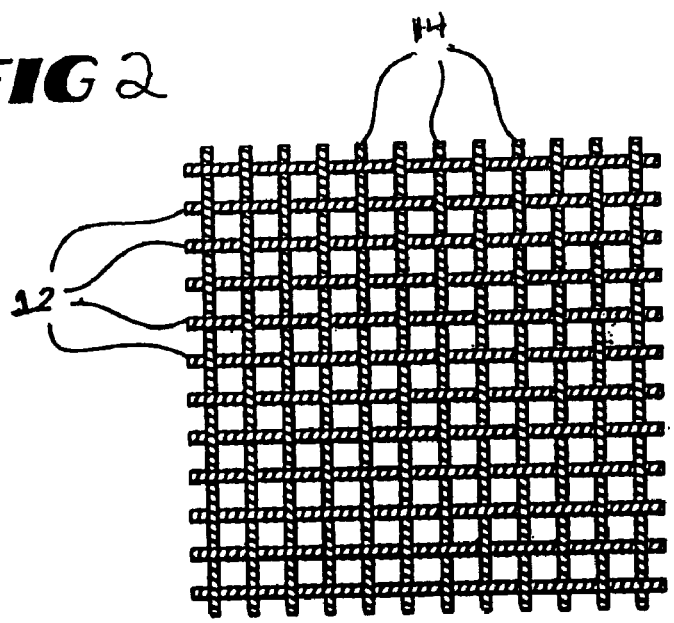
FIG. 3 is a schematic showing of a conventional weave pattern useful in the textile structure of the present invention.
Figure 4:
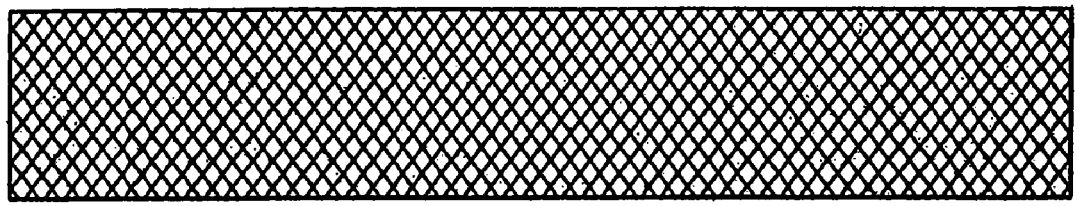
FIG. 4 is a side elevation view of a braided vascular graft of the present invention.
Figure 4:
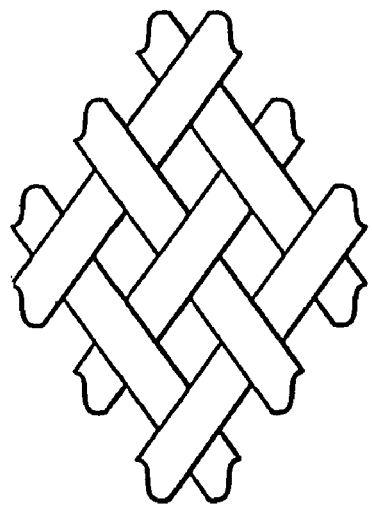
Figure 4:
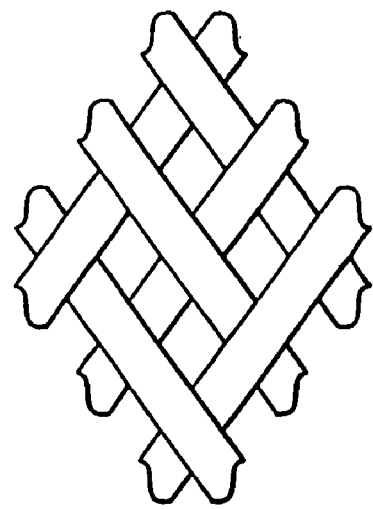
Figure 4:
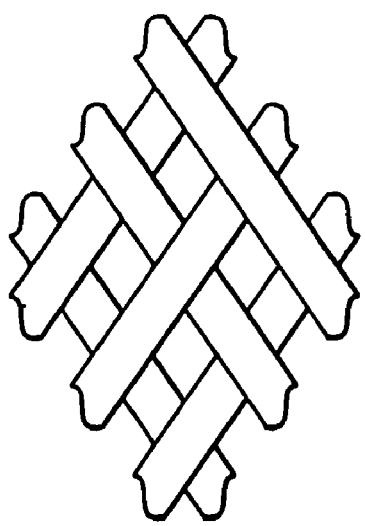

FIG. 2 is a perspective view of a vascular graft with a woven textile structure as used in the present invention. FIG. 3 shows magnified view of the woven pattern of the graft of FIG. 2. Any known weave patterns for the fabric layer may be used, including simple weaves, basket weaves, twill weaves, velour weaves, and the like. The weave pattern includes warp yarns 12 running along the longitudinal length (L) of the woven product and fill yarns 14 running around the circumference (C) of the woven product. The warp and fill yarns are at approximately 90 degrees to one another, with fabric flowing from the machine in the warp direction.

Braiding may also be used, as shown for example in FIGS. 4 and 4A-4C. Braiding of yarns includes the interlacing of two yarn systems; such as the pass of the yarns being diagonal to the fabric delivery direction, and forming either a flat or a tubular structure. Useful braids include an interlocking three-dimensional braid and a solid three-dimensional braid. A multi-layered braided structure is also contemplated and is defined as a structure formed by braiding wherein the structure has a plurality of distinct and discrete layers. These layers may be bound by interlocking yarns or by adhesive laminates, sewing or the like.

Figure 5:
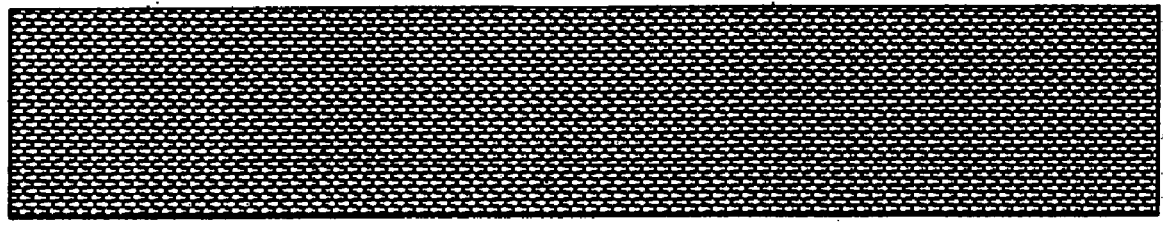
FIG. 5 is a side elevational view of a knitted vascular graft contemplated as the textile material in the present invention.
Figure 5A:
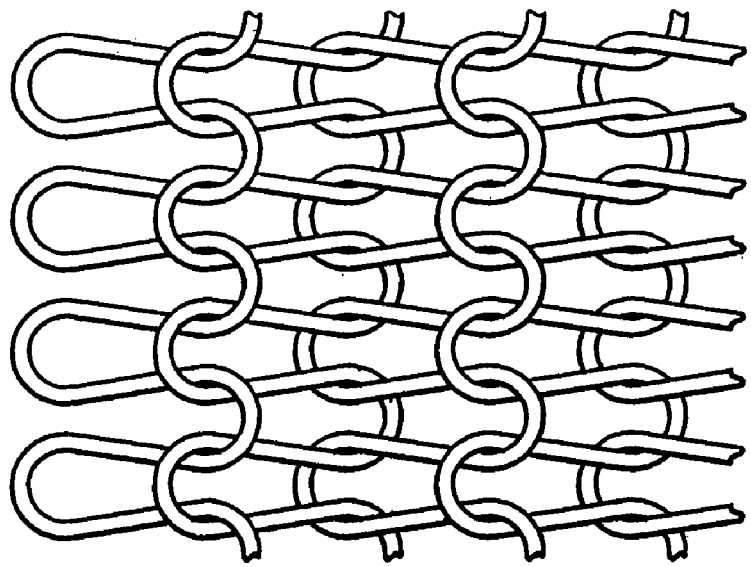
FIG. 5A is an enlarged detail of FIG. 5.

Additionally, knitted fabrics as shown in FIGS. 5 and 5A may be used as the textile material. Knitting involves the inter-looping of one yarn system into vertical columns and horizontal rows of loops called wales and courses, respectively; the fabric coming out of the machine in the wale direction.

Preferably, the yarns of the textile of the material are made from thermoplastic materials including, but not limited to, polyesters, polypropylenes, polyethylenes, polyurethanes, polynaphthalenes, polytetrafluoroethylenes, and the like. A preferred embodiment uses polyethyleneterephthalate (PET) as the textile material. The yarns may be of the multifilament, monofilament, or spun-types. In most vascular applications, multifilaments are preferred due to the increase in flexibility. Where enhanced crush-resistance is desired, the use of monofilaments have been found to be effective. As is well know, the type and denier of the yarn chosen are selected in the manner which forms a pliable soft tissue prosthesis, and, more particularly, a vascular structure.

The blood tight properties of the textile material of the present invention may be used in other applications besides vascular grafts. The blood tight implantable textile material may be used in many applications where it is desirable that an initially blood tight material may be needed; but also a material which further allows assimilation in the host body as the biodegradable impregnated material biodegrades in the body. A preferred embodiment is as a vascular patch. A vascular patch may be constructed of a thin layer membrane of the implantable textile material which is generally in an elongate planar shape. As is well know, a vascular patch may be used to seal an incision in the vascular wall or otherwise repair a soft tissue area in the body. The textile surface is desirable in such applications so as to promote cellular ingrowth and healing. Hernia patches are also contemplated.

In a preferred embodiment of the present invention, the non-colloidal mono-polymeric mixture includes a polysaccharide, alcohol and water. The alcohol is preferably ethanol, making the polysaccharide more soluble in the water solution. Many different polysaccharides may be used in the present invention, including, but not limited to, algin, carboxymethylcelluose, tarrageenan, furcellaran, agarose, guar, locust bean gum, gum Arabic, carboxymethylcellulose, hydropropyl cellulose, methyl cellulose, and the like. In a preferred embodiment, sodium alginate is used as the polysaccharide.

Sodium alginate is particularly desirable as it is readily available and attainable from seaweed. Algenic acid and its derivatives are manufactured commercially involving several operations including extraction and purification from seaweed, utilizing ion-exchange reactions.

Preferably, the non-colloidal polymeric mixture is bioresorbable. The implantable textile material preferably at first is blood tight but over time the non-colloidal mono-polymeric mixture degrades within the body and is reabsorbed by the body as the textile material is assimilated, i.e. in growth within the porous structure, incorporating it into the host body. The human body can degrade and uptake the alginate harmlessly. Typically, an alginate will reabsorb into the body in a four week period. Collagen is typically absorbed into the body in a six week period. This is another advantageous feature highlighting algins usefulness vis-à-vis collagen and other proteinaceous In an alternative embodiment, the alginate may be chemically cross-linked to form a non-removable material. The cross-linking forms a more stable component which would not be readily absorbed in the body or may be reabsorbed in the body over a longer period of time. The amount of cross-linking of the component may custom tailor the implantable material to a desired amount of degrading time. The mixture of the present invention can be cross-linked in several ways. For example, formation of claravelent bonds within the polysaccharide matrix can produce generally irreversible cross-linking. Alternatively, the mixture of the present invention can be cross-linked by the formation of ionic bonds within the polysaccharide. In another example, cross-links may be formed from the polysaccharide of the invention through weaker intermolecular interactions, such as, for example, hydrogen bonding and specific van der Waals interactions.

For purposes of this invention, the specific porosity of the material can be measured with a Wesolowski porosity tester. With this apparatus, a graft is tied off at one end and the free end is attached to a valve on a porometer so that the graft hangs freely in a vertical position. Then, water is run through the graft for one minute and all the water that escapes from the graft is collected and measured. The specific porosity of the graft is then calculated according to the following formula:

$$D = \frac{V}{A}$$

where V is the volume of water collected in ml/min and A is the surface area of the graft exposed to water in cm². A specific porosity of less than or equal to 1.0 ml/min/cm² is considered an acceptable amount of leaking for an implantable vascular graft. Accordingly, for purposes of this invention, a substantially blood tight graft means a graft with a specific porosity of impregnation of less than 1.0 ml/min/cm².

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of making a blood-tight implantable textile material comprising:
   providing an unmodified textile material;
   mixing a polysaccharide with water and an alcohol to form a non-colloidal mono-polymeric mixture; and
   saturating said textile material with said mixture.

2. A method according to claim 1 wherein said textile material is selected from the group consisting of woven, knitted, braided, velour, and felts.

3. A method according to claim 2 wherein said textile is a porous woven structure.

4. A method according to claim 3 wherein said non-colloidal mixture saturates pores of said porous woven structure.

5. A method according to claim 1 wherein said textile material is an artificial vascular graft.

6. A method according to claim 1 wherein said polysaccharide is an alginate.

7. A method according to claim 6 wherein said alginate is bioresorbable within the body after implantation.

8. A method according to claim 6 wherein said alginate is crosslinked and is non-resorbable.

9. A method according to claim 1 wherein said blood-tight implantable textile material has a porosity of impregnation of less than about 1.0 ml/min/cm².

10. A method according to claim 9 wherein said mixture is saturated within said textile material by massaging said mixture into pores of said unmodified textile material.

11. A blood-tight textile material implantable in a mammal comprising:
    an unmodified textile material having a porous structure,
    a non-colloidal mono-polymeric mixture saturated within said porous structure of said textile material to make it substantially non-porous, said non-colloidal mixture comprising a polysaccharide, an alcohol, and water.

12. A blood-tight textile material according to claim 11 wherein said polysaccharide is an alginate.

13. A textile material according to claim 11 wherein said blood-tight textile material is a vascular graft.

14. A blood-tight textile material according to claim 11 wherein said textile material is selected from the group consisting of woven, knitted, velour and felts.

15. A blood-tight textile material according to claim 14 wherein said textile is a porous woven structure.

16. A blood-tight textile material according to claim 15 wherein said non-colloidal mixture saturates pores of said porous woven structure.

17. An artificial vascular graft comprising:
    a tubular structure comprising an unmodified textile structure impregnated with a non-colloidal mono-polymeric mixture comprising sodium alginate, an alcohol, and water.

18. An artificial vascular graft according to claim 17 wherein said graft further comprises a stent disposed circumferentially interior to said tubular structure.

19. An artificial vascular graft according to claim 17 wherein said textile structure is selected from the group consisting of, woven structure, knitted structure, and braided structures.

* * * * *

UNITED STATES PATENT AND TRADEMARK OFFICE
CERTIFICATE OF CORRECTION

PATENT NO. : 7,329,531 B2 Page 1 of 1
APPLICATION NO. : 10/734785
DATED : February 12, 2008
INVENTOR(S) : Steve Keenan It is certified that error appears in the above-identified patent and that said Letters Patent is hereby corrected as shown below:

On the cover page at (74), Attorney, Agent or Firm, the printed patent incorrectly reads "...Hoffman & Baron, LLP..."; the patent should read --Hoffmann & Baron, LLP--.

At column 4, line 60, the printed patent incorrectly reads "..." non-colloidal mon-polymeric" as used..."; the patent should read --..."non-colloidal mono-polymeric" as used...--.

At column 5, line 65, the printed patent incorrectly reads "...well know, the type and denier..."; the patent should read --...well known, the type and denier...--.

At column 6, line 11, the printed patent incorrectly reads "...As is well know, a vascular patch..."; the patent should read --...As is well known, a vascular patch...--.

At column 6, line 44, the printed patent incorrectly reads "...collagen and other proteinaceous..." the patent should read --...collagen and other proteinaceous derivatives...--.

Signed and Sealed this

Tenth Day of June, 2008

JON W. DUDAS
*Director of the United States Patent and Trademark Office*